US010682293B2

(12) United States Patent
Alvarez et al.

(10) Patent No.: US 10,682,293 B2
(45) Date of Patent: *Jun. 16, 2020

(54) AEROSOL ANTIPERSPIRANT PRODUCT

(71) Applicant: Conopco, Inc., Englewood Cliffs, NJ (US)

(72) Inventors: Sebastian Alvarez, Follifoot (GB); Kevin Ronald Franklin, Wirral (GB); Philip Christopher Waterfield, Heswall (GB)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/772,675

(22) PCT Filed: Nov. 1, 2016

(86) PCT No.: PCT/EP2016/076306
§ 371 (c)(1),
(2) Date: May 1, 2018

(87) PCT Pub. No.: WO2017/076836
PCT Pub. Date: May 11, 2017

(65) Prior Publication Data
US 2018/0311119 A1 Nov. 1, 2018

(30) Foreign Application Priority Data
Nov. 6, 2015 (EP) .................................... 15193404

(51) Int. Cl.
| | |
|---|---|
| *A61K 8/04* | (2006.01) |
| *A61K 8/26* | (2006.01) |
| *A61Q 15/00* | (2006.01) |
| *A61K 8/19* | (2006.01) |
| *A61K 8/44* | (2006.01) |
| *A61K 8/58* | (2006.01) |
| *B65D 83/44* | (2006.01) |
| *B05B 7/04* | (2006.01) |
| *B65D 83/14* | (2006.01) |

(52) U.S. Cl.
CPC ............ *A61K 8/046* (2013.01); *A61K 8/19* (2013.01); *A61K 8/26* (2013.01); *A61K 8/44* (2013.01); *A61K 8/585* (2013.01); *A61Q 15/00* (2013.01); *B65D 83/44* (2013.01); *A61K 2800/31* (2013.01); *A61K 2800/87* (2013.01); *B05B 7/0483* (2013.01); *B65D 83/752* (2013.01)

(58) Field of Classification Search
None
See application file for complete search history.

(56) References Cited

U.S. PATENT DOCUMENTS

| | | |
|---|---|---|
| 2,210,013 A | 8/1940 | Teller |
| 2,412,535 A | 12/1946 | Richardson et al. |
| 3,666,668 A | 5/1972 | Klausner |
| 3,766,233 A | 10/1973 | Tsukada |
| 3,792,068 A | 2/1974 | Luedders et al. |
| 4,183,911 A | 1/1980 | Smithies et al. |
| 4,359,456 A | 11/1982 | Gosling et al. |
| 4,369,173 A | 1/1983 | Causland et al. |
| 4,435,382 A | 3/1984 | Shin et al. |
| 5,348,731 A | 9/1994 | Patti et al. |
| 5,744,130 A | 4/1998 | Guskey et al. |
| 5,814,309 A | 9/1998 | Panitch |
| 5,911,977 A | 6/1999 | Brewster et al. |
| 5,955,065 A | 9/1999 | Thong et al. |
| 6,024,945 A | 2/2000 | Parekh |
| 6,042,816 A | 3/2000 | Shen |
| 6,096,297 A | 8/2000 | Jones et al. |
| 6,136,303 A | 10/2000 | Ruebusch et al. |
| 6,261,543 B1 | 7/2001 | Fletcher et al. |
| 6,383,476 B1 | 5/2002 | Scavone et al. |
| 6,511,243 B2 | 1/2003 | Miranda |
| 7,087,220 B2 | 8/2006 | Li |

(Continued)

FOREIGN PATENT DOCUMENTS

| | | |
|---|---|---|
| CN | 1323191 | 11/2001 |
| DE | 19962878 | 6/2001 |

(Continued)

OTHER PUBLICATIONS

Search Report and Written opinion in PCTEP2019055000; dated Apr. 3, 2019.
IPRP in PCTEP2016080034 ; Feb. 14, 2018.
Search Report and Written Opinion in EP17199987; dated Dec. 6, 2017.
Written Opinion in PCTEP2015074529; dated Sep. 6, 2016.
IRPR2 in PCTEP2015074529; dated Dec. 2, 2016.
IRPR2 in PCTEP2015074528; Jan. 18, 2017.
Search Report & Written Opinion in PCTEP2016080034; dated Feb. 9, 2017.
Karl Laden; Chemistry of Aluminum-Zirconium-Glycine (AZG) Complexes; Antiperspirants and Deodorants; 1999; pp. cover pages, title pages & p. 137 (total of 4 pages); vol. 20, Second Edition.

(Continued)

*Primary Examiner* — Jessica Worsham
(74) *Attorney, Agent, or Firm* — Greenberg Traurig, LLP

(57) ABSTRACT

An antiperspirant aerosol product having good sustainability characteristics and comprising an anhydrous antiperspirant aerosol composition comprising particulate antiperspirant active suspended in a carrier oil, the ratio of propellant to base composition being from 2:1 to 4:1 by weight and an aerosol dispenser comprising a container body, an aerosol valve, and a valve actuator; characterised in that the particulate antiperspirant active comprises a basic aluminium chloride compound of formula $Al_2(OH)_{4.4}Cl_{1.6}$ to $Al_2(OH)_{4.9}Cl_{1.1}$, water soluble calcium salt and an amino acid and the aerosol valve of the aerosol dispenser has a vapor phase tap (VTP) to restrictive tailpiece (RTP) ratio of from 0.6:1 to 1.2:1.

11 Claims, No Drawings

(56) References Cited

U.S. PATENT DOCUMENTS

| | | | |
|---|---|---|---|
| 7,704,531 | B2 | 4/2010 | Tang et al. |
| 9,775,791 | B2 | 10/2017 | Fawzy et al. |
| 9,867,765 | B2 | 1/2018 | Franklin |
| 10,117,814 | B2 | 11/2018 | Duncan |
| 2002/0012565 | A1 | 1/2002 | Sirna et al. |
| 2002/0125462 | A1 | 9/2002 | McKie et al. |
| 2003/0049219 | A1 | 3/2003 | Lemoine et al. |
| 2003/0215399 | A1 | 11/2003 | Smith et al. |
| 2003/0215408 | A1 | 11/2003 | Dees |
| 2004/0115147 | A1 | 6/2004 | Vu et al. |
| 2005/0163737 | A1 | 7/2005 | Lemoine et al. |
| 2006/0153788 | A1 | 7/2006 | Swaile et al. |
| 2006/0204463 | A1 | 9/2006 | Tang et al. |
| 2006/0222612 | A1 | 10/2006 | Ni et al. |
| 2007/0020211 | A1 | 1/2007 | Li et al. |
| 2007/0148113 | A1 | 6/2007 | Lemoine et al. |
| 2007/0148443 | A1 | 6/2007 | Blum et al. |
| 2007/0172440 | A1 | 7/2007 | Schulz et al. |
| 2007/0196303 | A1 | 8/2007 | Li et al. |
| 2007/0286830 | A1 | 12/2007 | Li et al. |
| 2007/0292358 | A1 | 12/2007 | Emmerling et al. |
| 2008/0131354 | A1 | 6/2008 | Li et al. |
| 2008/0241089 | A1 | 10/2008 | Banowski et al. |
| 2008/0267895 | A1 | 10/2008 | Franklin et al. |
| 2009/0018044 | A1 | 1/2009 | Dreja et al. |
| 2009/0104281 | A1 | 4/2009 | Taylor et al. |
| 2009/0232746 | A1 | 9/2009 | Mateu et al. |
| 2009/0311195 | A1 | 12/2009 | Clark et al. |
| 2009/0317347 | A1 | 12/2009 | Popoff et al. |
| 2010/0303749 | A1 | 12/2010 | Pan |
| 2011/0038822 | A1 | 2/2011 | Phipps et al. |
| 2011/0217254 | A1 | 9/2011 | Miertsch et al. |
| 2011/0274637 | A1 | 11/2011 | Milardovic et al. |
| 2013/0164238 | A1 | 6/2013 | Banowski et al. |
| 2013/0273274 | A1 | 10/2013 | Mueller et al. |
| 2014/0079649 | A1 * | 3/2014 | Swaile .......... A61K 8/0241 424/47 |
| 2014/0173833 | A1 | 6/2014 | Banowski et al. |
| 2014/0178321 | A1 | 6/2014 | Banowski et al. |
| 2014/0301963 | A1 | 10/2014 | Claas et al. |
| 2015/0118173 | A1 | 4/2015 | Farwick et al. |
| 2016/0106649 | A1 | 4/2016 | Fawzy et al. |
| 2016/0113850 | A1 | 4/2016 | Fawzy et al. |
| 2018/0140522 | A1 | 5/2018 | Doering et al. |

FOREIGN PATENT DOCUMENTS

| | | | |
|---|---|---|---|
| EP | 0308937 | | 3/1989 |
| EP | 0343843 | | 11/1989 |
| EP | 0405598 | | 1/1991 |
| EP | 0674899 | | 10/1995 |
| EP | 1175165 | | 4/2000 |
| EP | 1104282 | | 6/2001 |
| EP | 1550435 | | 7/2005 |
| EP | 1576946 | | 9/2005 |
| EP | 2481392 | | 8/2012 |
| EP | 2999452 | | 12/2017 |
| GB | 811079 | | 4/1959 |
| GB | 813767 | | 5/1959 |
| GB | 1024501 | | 3/1966 |
| GB | 1268200 | | 3/1972 |
| GB | 1285073 | | 8/1972 |
| GB | 1347950 | | 2/1974 |
| GB | 1362495 | | 8/1974 |
| GB | 1555044 | | 11/1979 |
| GB | 1589229 | | 5/1981 |
| GB | 2113116 | | 8/1983 |
| GB | 2299507 | | 10/1996 |
| JP | 2014047186 | | 3/2014 |
| WO | WO9604884 | | 2/1996 |
| WO | WO9624326 | | 8/1996 |
| WO | WO-0001422 A1 * | | 1/2000 .......... A61L 9/14 |
| WO | WO0010512 | | 3/2000 |
| WO | WO0127351 | | 4/2001 |
| WO | WO2005007377 | | 1/2005 |
| WO | WO2005018553 | | 3/2005 |
| WO | WO2005105026 | | 11/2005 |
| WO | WO2006050776 | | 5/2006 |
| WO | W02006062846 | | 6/2006 |
| WO | WO2006091417 | | 8/2006 |
| WO | WO2007124889 | | 11/2007 |
| WO | WO2008063188 | | 5/2008 |
| WO | WO2009044381 | | 4/2009 |
| WO | WO2009075678 | | 6/2009 |
| WO | WO2009076591 | | 6/2009 |
| WO | WO2011016807 | | 2/2011 |
| WO | WO2012010684 | | 1/2012 |
| WO | WO2012021356 | | 2/2012 |
| WO | WO2012060817 | | 5/2012 |
| WO | WO2012061280 | | 5/2012 |
| WO | WO2012098189 | | 7/2012 |
| WO | WO2012148480 | | 11/2012 |
| WO | WO2012148481 | | 11/2012 |
| WO | WO2013064367 | | 5/2013 |
| WO | WO2013158077 | | 10/2013 |
| WO | WO2014095688 | | 6/2014 |
| WO | WO2014147739 | | 9/2014 |
| WO | WO2014187684 | | 11/2014 |
| WO | WO2014187685 | | 11/2014 |
| WO | WO2014187802 | | 11/2014 |
| WO | WO2015091742 | | 6/2015 |
| WO | WO2016066528 | | 5/2016 |
| WO | WO2016078991 | | 5/2016 |
| WO | WO2016198202 | | 12/2016 |
| WO | WO2017076836 | | 5/2017 |

OTHER PUBLICATIONS

Search Report in EP14190531; dated May 8, 2015.
Search Report in EP14193902; dated May 6, 2015.
Written Opinion in EP14193902; dated May 6, 2015.
Written Opinion in EP14190531; dated May 8, 2015.
IPRP2 in PCTEP2014059583; Sep. 11, 2015.
Written Opinion 2 in PCTEP2014060306; dated May 8, 2015.
Written Opinion in EP13168417; dated Oct. 31, 2013.
Written Opinion in EP13168418; dated Oct. 31, 2013.
IPRP2 in PCTEP2014060306; Sep. 16, 2015.
Search Report in EP13168418; dated Oct. 31, 2013.
Search Report in EP13168417; dated Oct. 31, 2013.
Laden; Antiperspirants and Deodorants 1999 2nd Edition pp. 96-97;
Antiperspirants and Deodorants 1999 2nd Edition pp. 96-97; 1999; pp. 96-97; 2nd Edition.
Search Report & Written Opinion in PCTEP2015074529; dated Dec. 21, 2015.
Pluronic(R) F-127; Newdruginfo.com; Jun. 7, 2016; 1 page.
Written Opinion 2 in PCTEP2014059583; dated Apr. 30, 2015.
Search Report & Written Opinion in PCTEP2015076365; dated Feb. 11, 2016.
Search Report & Written Opinion in PCTEP2015074528; dated Jan. 20, 2016.
Written Opinion in EP14190530; dated Feb. 12, 2015.
Search Report in EP14190530; dated Feb. 12, 2015.
Notice of Opposition in EP14725433 (EP2999452) (P&G); Sep. 24, 2018.
Clinical Protection Antiperspirant Deodorant Cream; Deodorant Cream Product Data Sheets (D20A-D); Sep. 24, 2018; pp. 1-11.
Deodorant Roll-on; Deodorant Roll-on Product Data Sheets (D19A-J) ; Apr. 1, 2011; pp. 1-31.
Written Opinion in PCTEP2014060306; dated Oct. 6, 2014.
Search Report in PCTEP2014059583; dated Oct. 6, 2014.
Written Opinion in PCTEP2014059582; dated Oct. 6, 2014.
Search Report in PCTEP2014060306; dated Oct. 6, 2014.
Search Report in PCTEP2014059582; dated Oct. 6, 2014.
Written Opinion 1 in PCTEP2014059583; dated Oct. 6, 2014.
Search Report and Written Opinion in EP18164854; dated Jul. 30, 2018.
Search Report and Written Opinion in EP17200556; dated Apr. 11, 2018.

(56) References Cited

OTHER PUBLICATIONS

Amodimethicone; Saapedia; May 21, 2015; pp. 1-3; "www.saapedia.org/en/saa/?type-detail&id-1885".; .; United States of America.
Search Report & Written Opinion in PCTEP2015075419; dated Jan. 21, 2016.
Apr. 2014 Teachers Guide for (Under) Arm Yourself with Chemistry!; acs.orgichemmatters; Apr. 2014; pp. 1-38 Retrieved from Internet: http://www.acs.org/content/dam/acsorg/education/resources/highschool/chemmatters/teacherguide/chemmatters-tg-april2014-deodorant.doc retrieved Dec. 17, 2015 XP055234066.
Anonymous; Aluminum Zirconium Chlorohydrex Complexes with Glycine; Cosmeticsinfo.org; 2015; pp. 1-3 Retrieved from the Internet: http://www.cosmeticsinfo.org/ingredient/aluminum-zirconium-chlorohydrex-complexes-glycine [retrieved on Dec. 7, 2015] XP055234010.
Anti-Perspirant Deodorant Roll-on; Mintel GNPD Database; Nov. 1, 2014; pp. 1-2; XP002739560; Germany.
Anti-Perspirant Deodorant Roll-on; Mintel GNPD Database; Apr. 1, 2012; pp. 1-2; XP002739559; United Kingdom.
Search Report in EP15150655; dated Jun. 22, 2015; European Patent Office (EPO).
Written Opinion in EP15150655; dated Jun. 22, 2015; European Patent Office (EPO).
Search Report and Written Opinion in PCTEP2018079947; dated Jan. 2, 2019.
Protective Deodorant Spray, Mintel GNPD, 2014, pp. 1-2; XP002756659.
Written Opinion 2 in PCTEP2016076306, dated Sep. 14, 2017.
IPRP2 in PCTEP2016076306, Dec. 4, 2017.
Search Report & Written Opinion in EP15193404, dated May 9, 2016.
Search Report & Written Opinion in EP15193409, dated Apr. 18, 2016.
Search Report & Written Opinion in PCTEP2016076311, dated Dec. 23, 2016.
Search Report & Written Opinion in PCTEP2016076306, dated Jan. 23, 2017.
Co-Pending Application, Kevin Ronald Franklin, Filed May 1, 2018.
Co-Pending Application, Sebastian Alvarez, Filed May 1, 2018.
Mintel GNPD; Sensitive Skin Deodorant Spray, Lactovit; Mintel GNPD; Jul. 2013; pp. 1-3, Record ID 2102829.
Mintel GNPD; Protective Deodorant, Lactovit Activit; Mintel GNPD; Sep. 2013; pp. 1-3 Record ID 2192256.
Mintel GNPD; Repairing Deodorant, Lactoit Lacourea 10; Mintel GNPD; Aug. 2014; pp. 1-2 Record ID 2619709.
Mintel GNPD; Deodorant Extra-Efficiency, Lactovit Original; Mintel GNPD; Jul. 2013; pp. 1-2 Record ID2121626.
Edited by Barel, et al.; Handbook of Cosmetic Sience and Technology; Handbook of Cosmetic Sience and Technology; Apr. 9, 2014; pp. 1-2 (Cover & summary); 4th Edition.
Edited by Barel, et al.; Section 48—Antiperspriants and Section 49—Deodorants; Handbook of Cosmetic Science and Technology; Apr. 9, 2014; pp. 1-19 (cover pp. and pp. 505-518; 4th Ed.
Regulations; Official Journal of the European Union; Mar. 9, 2012; pp. 1-295 or L83/1-L83/295.

* cited by examiner

AEROSOL ANTIPERSPIRANT PRODUCT

This invention relates to antiperspirant products, more particularly to aerosol antiperspirant products in the form of high efficacy concentrated compositions in suitably adapted dispensers.

Aerosols account for a significant portion of the antiperspirant products on the market. In many countries, aerosols are a preferred form of antiperspirant product, outselling sticks and roll-ons. With the development of emerging markets and increases in the proportion of the population purchasing antiperspirant products, it is expected that the demand for antiperspirant products, including aerosol antiperspirant products, will increase.

In the face of increased global demands, environmental sustainability has become a matter of increasing interest. In aerosol applications, concentrates have the potential to benefit both manufacturers and the environment. Aerosol concentrates offer manufacturers cost advantages in terms of reduced packaging (both primary and secondary), reduced propellant use, reduced shipping costs, and the like. The environment is benefited by a product that, compared to conventional aerosols, emits less propellant and as a consequence less volatile organic compounds [VOCs]), generates less packaging waste and, uses less metal, in particular aluminium, both in the container and in the composition.

GB 2,299,507 A (Unilever) discloses low flow rate propellant driven antiperspirant compositions comprising less than 60% by weight of a propellant and an initial spray rate of no more than 0.5 g/s.

EP 674,899 B1 (Unilever) discloses concentrated deodorant compositions comprising propellant, most preferably at 30-60% by weight of the composition, and having a discharge valve adapted to allow the composition to be sprayed at an initial spray rate of less than 0.3 g/s.

EP 343,843 A2 (Mennen) discloses aerosol antiperspirant compositions comprising substantivity fluid, capable of being sprayed at reduced spray rate.

GB 1,589,229 (J. G. Spitzer et al) discloses aerosol antiperspirant compositions delivering high active concentration of astringent salt at low delivery rate with good adherence to skin.

GB 1,555,044 (J. G. Spitzer et al) discloses high active content aerosol compositions delivered at low spray rate.

Consumer habits and perceptions can be exceedingly difficult to change. If a product does not fit conventional spray habits, consumer acceptance of that product may be difficult, no matter how good the product. Conversely, a product that matches consumer behavior but does not deliver on efficacy and sensory requirements is unlikely to be commercially accepted. When providing antiperspirant products in concentrated form, reference needs be made to the manner in which aerosol antiperspirants are typically used. A typical spray period, by which is meant the time during which an actuator is actively engaged to dispense product, is typically on the order of one half to 2 seconds.

Concentrated aerosol base compositions can be less tolerant of over-application than standard dilute product bases. In addition to potential sensory negatives, over-application of concentrated aerosol base compositions can result in deposition of excess antiperspirant (AP) active as a white, powdery residue on the skin as well as clothing in contact with the underarm, a significant problem in the eyes of many consumers. Reducing the level of AP active in the composition can in part reduce this latter problem; however, it is difficult to do this without detrimentally affecting the antiperspirancy performance.

Producing an acceptable aerosol concentrate requires more than simply changing the level of active, since irrespective of active level, consumers prefer their usual application habits. Minimizing spray rate is another approach to managing concentrates. Typical spray rates for powder aerosols are of the order of 0.7 g/s to 1.2 g/s, but lower rates may be desirable for concentrated aerosols. Minimizing spray rate theoretically requires little or no disruption to consumer behavior, because the same dose can then be applied in approximately the same time, despite the aerosol being more concentrated. However, reducing spray rate presents numerous issues for product engineers. As a practical matter, reducing spray rate can exacerbate nozzle clogging and increase spluttering, particularly in the context of antiperspirant aerosol compositions with higher active levels. Additionally, reduced spray rates present challenges in terms of providing compositions that provide acceptable sensory properties, given the confines of consumer application habits and typical application spray periods. Reduced spray rate can also result in reduced product efficacy if insufficient active is dispensed.

There remains a need for concentrated antiperspirant aerosol products that provide a combination of desirable efficacy properties and dispensing properties.

One object of this invention is to provide a more environmentally sustainable aerosol product, in particular, a concentrated aerosol antiperspirant product. Another object of this invention is to provide a concentrated aerosol antiperspirant product that delivers desirable efficacy and sensory properties without disruption to existing spray habits of consumers. In particular, it is desirably to have good efficacy without encountering problems with white marks on the skin or clothing. Yet another aspect of this invention is to provide a concentrated aerosol product having desirable dispensing properties.

It has now been found that by specifying particular parameters, concentrated aerosol antiperspirant products meeting one or more objects of this invention may be provided.

In a first aspect of the invention, there is provided an antiperspirant aerosol product comprising:

A) an anhydrous antiperspirant aerosol composition comprising a propellant and a base composition, the base composition comprising particulate antiperspirant active suspended in a carrier oil, the ratio of propellant to base composition being from 2:1 to 4:1 by weight and B) an aerosol dispenser comprising: a container body, an aerosol valve, and a valve actuator;

characterised in that the particulate antiperspirant active comprises a basic aluminium chloride compound of formula $Al_2(OH)_{4.4}Cl_{1.6}$ to $Al_2(OH)_{4.9}Cl_{1.1}$, water soluble calcium salt and an amino acid; and the aerosol valve of the aerosol dispenser has a vapor phase tap (VTP) to restrictive tailpiece (RTP) ratio of from 0.6:1 to 1.2:1.

In a second aspect of the invention, there is provided the use of an antiperspirant aerosol product according to the first aspect of the invention to give an antiperspirancy benefit on the surface of the human body.

In a further aspect of the invention, there is provided a method of achieving an antiperspirancy benefit comprising the application to the surface of the human body of an anhydrous antiperspirant aerosol composition comprising a propellant and a base composition, the base composition comprising particulate AP active suspended in a carrier oil, the ratio of propellant to base composition being from 2:1 to 4:1 by weight, said application being performed using an aerosol dispenser comprising: (i) a container body; (ii) an aerosol valve, and (iii) a valve actuator; characterised in that the ratio of propellant to antiperspirant base is from 2:1 to 4:1 by weight and in that the aerosol valve of the aerosol dispenser has a vapor phase tap (VTP) to restrictive tailpiece (RTP) ratio of from 0.6:1 to 1.2:1.

In a further aspect of the present invention, there is provided the manufacture of an antiperspirant aerosol product according to the first aspect of the invention, the anhydrous antiperspirant aerosol composition being placed within the container body of the aerosol dispenser.

Use of the present invention involves the anhydrous antiperspirant aerosol composition being (topically) applied to the surface of the human body using the aerosol dispenser. In so doing, significant sustainability benefits ensue, compared with the use of conventional antiperspirant aerosol products.

Preferably, the product has a mean spray rate of from 0.3 to 0.55 g/sec., more preferably 0.3 g/s to 0.5 g/s and most preferably from 0.35 to 0.45 g/s. Obtaining such spray rates is highly preferred because they enable the consumer to spray the aerosol composition for approximately the same time as they would spray a convention aerosol composition without applying excessive amounts of the composition. Hence, optimizing the spray rate enables efficient usage of the formulation and helps avoid problems such as white marks, which excessive application can cause.

By selecting parameters in accordance with the aspects of the invention as described above, one attains a concentrated antiperspirant aerosol product of surprisingly good antiperspirancy efficacy and excellent environmental sustainability. In particular, it has been found that aluminium usage in the composition can be minimized and aluminum or other metal usage in the can container can be minimized, in addition to minimizing VOC usage.

Herein, the abbreviation "AP" stands for antiperspirant.

Herein, the term "mean spray rate" refers to the delivery rate of freshly made aerosol product as determined by the procedure described below. This procedure is described as the alternative procedure of FEA 643E of March, 2008 and is an average of the measurements obtained at 90%, 70%, 50%, 30% and 10% fill.

The spray rate of an aerosol product is determined by measuring the quantity of material expelled through the valve in a given time. The measurements are made with the dispenser and contents at 25° C. Measurements are taken at fill levels of 90%, 70%, 50%, 30%, and 10%, fill levels being determined by weight. At each fill level, the contents are sprayed for two periods of 5 seconds. The aerosol container body is vigorously shaken before each discharge. Weights of the aerosol product are taken before and after each discharge in order to calculate the amount discharged. This is divided by 5 to give a spray rate per second. The 10 spray rates measured according to this procedure are then averaged to give the mean spray rate. The dispenser and its contents may conveniently be kept at 25° C. by use of a water bath.

All references herein to ratios of propellant to antiperspirant base or ratios of propellant to AP active are the weight ratios of such component in a filled, freshly made dispenser prior to its first dispensing (herein referred to as a "fully charged" dispenser), and are on the basis of the AP active base and propellant totaling 100 weight percent. The base composition consists of all components of the aerosol compositions other than the propellant.

As used herein, the term "anhydrous" when used with reference to a composition means that no separate aqueous liquid phase is present and that the composition contains less than 1% by weight water, exclusive of any bound or complexed water that may be present in the raw materials, such as, for example, any water of hydration in the AP active. Preferably, such anhydrous compositions contains less than 0.5% by weight of water, and more preferably it is free from water, exclusive of any bound or complexed water that may be present in the raw materials, such as, for example, any water of hydration in the antiperspirant.

As used herein "volatile" describes a material having a measurable vapor pressure at 20° C.

As used herein, the abbreviation "BAC" stands for basic aluminium chloride compound.

In the following description of the preferred features of the antiperspirant composition, it should be understood that each preferred feature is independently preferred in combination with each of the preferred features of the dispenser herein described.

Antiperspirant aerosol compositions comprise two fractions: a first fraction that is the antiperspirant base (also referred to as the "base composition", "aerosol base composition", "aerosol base" or "base") and a second fraction that is the propellant.

During manufacture of an aerosol antiperspirant product, the antiperspirant base is commonly made by blending together all the composition ingredients other than the propellant, agitating the mixture to suspend the AP active in a carrier fluid, introducing the suspension into an aerosol container body, fitting a valve to the container, and pressurizing the container body by introduction of the propellant. In an alternative but related method, a partially formulated base is introduced to the container body and the base's remaining constituents are introduced into the container body to complete the base composition prior to fitting the valve and introducing propellant.

The particulate AP active employed in the present invention comprises a BAC of formula $Al_2(OH)_{4.4}Cl_{1.6}$ to $Al_2(OH)_{4.9}Cl_{1.1}$, a water-soluble calcium salt and an amino acid.

Preferably, the particulate AP active is predominately a BAC of formula $Al_2(OH)_{4.4}Cl_{1.6}$ to $Al_2(OH)_{4.9}Cl_{1.1}$, a water-soluble calcium salt and an amino acid.

Hereon, "predominately" should be understood to mean that the component or components is or are present at a level of greater than 90%, preferably greater than 95% and more preferably greater than 99% by weight.

More preferably, the particulate AP active employed in the present invention is solely a BAC of formula $Al_2(OH)_{4.4}Cl_{1.6}$ to $Al_2(OH)_{4.9}Cl_{1.1}$, a water-soluble calcium salt and an amino acid.

BACs of formula $Al_2(OH)_{4.4}Cl_{1.6}$ to $Al_2(OH)_{4.9}Cl_{1.1}$ are commercially available and are commonly known as aluminium sesquichlorohydrate (herein ASCH). They may be 'activated', that is to say increased in efficacy, by combination with a water soluble calcium salt and an amino acid, as described in WO 2014/187685 A1 (Unilever). The activated ASCH AP active obtained by such process is abbreviated as AASCH herein.

It should be noted that ASCH is a different BAC to the more commonly used AP active aluminium chlorohydrate (ACH), which has the formula $Al_2OH_5Cl$.

The particulate AP active comprising BAC of formula $Al_2(OH)_{4.4}Cl_{1.6}$ to $Al_2(OH)_{4.9}Cl_{1.1}$, water-soluble calcium salt and amino acid is preferably an AASCH prepared by heat activation of ASCH with a water-soluble calcium salt and an amino acid, preferably glycine.

Most commercial ASCH samples are of chemical formula $Al_2(OH)_{4.4}Cl_{1.6}$ to $Al_2(OH)_{4.9}Cl_{1.1}$ and such ASCH salts are preferred.

The BAC salt has aluminium to chloride molar ratio of from 1.25:1 to 1.82:1 and preferably 1.54:1 to 1.82:1.

In order for the AP active to attain high efficacy, it is important to have sufficient calcium present relative to the amount of aluminium present. The molar ratio of calcium to aluminium is typically at least 1:40, preferably at least 1:30 and more preferably at least 1:20. It is not advantageous to have the calcium concentration in excess of the aluminium concentration, indeed it is preferred that the calcium concentration is no more than half that of the aluminium concentration and more preferred that it is no more than a fifth of said concentration. For the preferred molar ratios of calcium to aluminium of at least 1:40 and at least 1:20, it is independently preferred that this ratio is no greater than 1:2, more preferred that it is no greater than 1:5 and most preferred that it is no greater than 1:7.

In particularly preferred embodiments, the molar ratio of calcium to aluminium in the AP active is from 1:20 to 1:7.

A preferred water-soluble calcium salt for use in the present invention is calcium chloride.

Herein, references to molar amounts and ratios of "aluminium" are calculated on the basis of mono-nuclear aluminium, but include aluminium present in poly-nuclear species; indeed, most of the aluminium in the salts of relevance is present in poly-nuclear species.

In order for the antiperspirant to become activated, it is important to have sufficient amino acid present relative to the amount of aluminium present. The molar ratio of amino acid to aluminium is preferably at least 1:20. It is not advantageous to have the amino acid concentration in excess of the aluminium concentration; hence, the molar amino acid to aluminium is preferably from 1:20 to 1:1 and more preferably from 1:20 to 1:4.

The presence of both calcium and amino acid is essential for the success of the present invention. In preferred embodiments, the molar ratio of calcium to aluminium is at least 1:40 and the molar ratio of amino acid to aluminium is at least 1:20. In further preferred embodiments the molar ratio of calcium to aluminium is at least 1:20 and the molar ratio of amino acid to aluminium is at least 1:10.

The above indicated preferences for calcium to aluminium molar ratio and/or amino acid to aluminium molar ratio may lead to compositions of higher Band III content (vide infra) and, in general, higher antiperspirancy performance.

It is noteworthy that an amino acid must be used in order to activate the antiperspirant salt. Preferred amino acids for use in the present invention are glycine, alanine, valine and proline. A particularly preferred amino acid for use in the present invention is glycine.

The activation process generally produces a mixture of aluminium species having a relatively high content of what is commonly termed Band III material, as determined by SEC (Size Exclusion Chromatography) analysis. The SEC technique employed is well known in the art and is described in further detail in U.S. Pat. No. 4,359,456 (Gosling). The SEC band commonly referred to as Band III is designated as "Peak 4" in EP 1,104,282 B1 by Gillette.

Herein, "Band III content" refers to the integrated area in the Band III region of the SEC chromatograph relative to the total integrated area in all of the regions corresponding to aluminium species; that is to say, Bands I, II, III, and IV.

In particular embodiments of the invention, compositions according to the invention preferably have a Band III content of at least 25% and more preferably at least 30%.

It is preferred that the AP active (mixture) is heated for sufficient time for the Band III content of the aluminium species to become at least 25% and more preferably at least 30%. This is preferably done prior to formulation into the final composition.

The particle size of the AP active may impact the extent to which a composition gives rise to white marks upon application. Larger particles of AP active can be more difficult to mask and more whitening than smaller particles. Large particles can also give rise to nozzle blockage, particularly at when present at high levels. Thus, it is often desirable to limit the amount of active present as relatively large particles. In one or more embodiments of the subject invention, the particles of AP active employed herein as a raw material, be the AP active complexed, activated, or otherwise, are of a size such that ≥99% by weight of such particles have a diameter that does not exceed 125 microns. In one embodiment of interest ≥99% by weight of the particles have a diameter below 100 microns. In another embodiment of interest, ≥95% by weight of the particles have a diameter below 75 microns.

From the perspective of volume average particle diameter, in at least one embodiment of this invention, the volume average particle diameter D50 (such particle diameter being sometimes referred to as the average particle size) is from 15 to 40 microns, more particularly 20 to 30 microns. Particle sizes and distributions are those that are obtained by laser light scattering, for example obtained from the appropriate Mastersizer instrument for anhydrous suspensions, obtainable from Malvern Instruments set to produce a volume plot. The instrument is employed with a lens selected in accordance with the maker's instructions to accommodate the expected particle size distribution, (or various lenses can be tested until the best lens is identified) and is preferably operated employing cyclomethicone (DC245™ from Dow Corning) as the liquid dispersant for a sample of the base composition to attain a particles concentration that achieves obscuration, i.e. 10-30% light scattered. Using the Polydisperse analysis model and knowing the dispersant RI, the RI of the particulate material and imaginary RI factor of 0.1, the plot of the particles size (d) distribution and the average particle size D50 is obtained.

The weight ratio of propellant to AP active is preferably from 5:1 to 10:1, more preferably from 6:1 to 9:1, and most preferably from 6:1 to 8:1. The preferred ratios of propellant to AP active enhance the benefits of the present invention as referred to above.

Herein, the propellant consists exclusively of the gaseous components of the composition, as they exist and 1 atmosphere pressure and 25° C. The antiperspirant base comprises a carrier oil in which the particulate materials of the base composition (in particular the AP active) are suspended. Such oils are liquid at 20° C. and are typically water-immiscible. It will be recognized that the carrier oil can provide one or more functions in addition to acting as a carrier; for example, some can act as emollients, mask active deposits or alter the appearance of the applied antiperspirant composition, and/or mask the odor of the composition itself or malodors generated by skin secretions. It will be further recognized that the water-immiscible carrier oil may be comprised of more than one type of oil. In one embodiment of this invention at least a portion of the water-immiscible oil comprises volatile oil, more particularly volatile silicone oil. In another embodiment of interest, at least a portion of the carrier oil comprises non-volatile oil.

In expressions relating to the amount of carrier oil present in the composition, it should be understood that it is the total amount of any such oils present that is referred to.

The amount of carrier oil in the composition is typically from 5 to 20% by weight of the total composition.

The ratio of carrier oil to AP active is preferably from 1:2 to 2:1 by weight and is more preferably from 1.2 to 1. This ratio is important to the sensory properties delivered by the invention and the reduced white marks or deposits.

The proportion of carrier oil in the base composition, including optional or other functional ingredients which are liquid at 20° C., is typically from 35 to 80% by weight, and in many embodiments is from 55 to 65% by weight, all based on the total weight of the base composition. In some embodiments it is desirable for the carrier oil to comprise at least 90%, more particularly at least 95% and, in one or more of the embodiments contemplated herein, at least 98% by weight of water-immiscible oil. The carrier oil may, but need not, comprise a combination of volatile as well as non-volatile oil, with the relative amounts thereof being selected based on the particular materials employed and the properties desired in the aerosol composition. In a number of embodiments the volatile oil comprises at least 30% by weight and, more particularly, at least 40% by weight of the carrier oil. In other embodiments, the carrier oil comprises at least 50% by weight and up to 80% by weight of volatile oil.

Among the volatile oils suitable for use herein are volatile silicone oils. The volatile silicone oils typically have a vapor pressure of from 10 Pa to 2 kPa at 25° C. Such volatile silicones can be linear or cyclic siloxanes, usually containing from 3 to 9 silicon atoms, and commonly from 4 to 6 silicon atoms, the silicon atoms being substituted by methyl groups, so that their alternative names are methicones and cyclomethicones. It is especially desirable to employ volatile silicone in which at least 80% by weight and particularly at least 90% contain at least 5 silicon atoms, such as cyclopentadimethylsiloxane (D5), cyclohexadimethylsiloxane (D6), dodecamethylpentasiloxane and tetradecamethylhexasiloxane. The cyclomethicone oils are especially preferred. Owing to their relatively low latent heat of evaporation, volatile silicone oils can evaporate without causing undue skin cooling. Additionally, such oils spread easily and tend to impart good sensory attributes.

The non-volatile oils suitable for use herein can be silicone oils and/or non-silicone oils. Non-volatile oils having a refractive index of at least 1.45 are of particular interest. Such oils in the base composition may advantageously lessen the appearance of visible residues on skin, not only immediately on application but also throughout the period (typically from 6 to 24 hours) before the antiperspirant composition is washed off.

Non-volatile silicone oils employed herein preferably contain one or more unsaturated substituents such as phenyl or diphenylethyl in replacement of the corresponding number of methyl substituents in polycyclosiloxanes or more preferably in linear siloxanes, often having 2 or 3 silicon atoms. Such non-volatile oils have a higher refractive index than that of the volatile silicone oils and tend to mask the AP active when it is deposited on skin. The non-volatile oils can also comprise dimethiconols which, as the name suggests, are hydroxyl-terminated.

The carrier oils can alternatively or additionally comprise one or more hydrocarbon oils, which can be either volatile or non-volatile. Suitable hydrocarbon oils include liquid aliphatic hydrocarbons such as mineral oils or hydrogenated polyisobutene, desirably selected to exhibit a low viscosity. Further examples of liquid hydrocarbons are polydecene and paraffins and isoparaffins of at least 10 carbon atoms.

Hydrocarbon oils conveniently comprise from 0 to 25%, more particularly from 0 to 15% by weight of the carrier oils.

In at least some advantageous embodiments, the carrier oils comprise liquid aliphatic or aromatic ester oils. Suitable aliphatic esters contain at least one long chain alkyl group, such as esters derived from $C_1$ to $C_{20}$ alkanols esterified with a $C_8$ to $C_{22}$ alkanoic acid or $C_6$ to $C_{10}$ alkanedioic acid. The alkanol and acid moieties or mixtures thereof are preferably selected such that they each have a melting point of below 20° C. Aliphatic esters include isopropyl myristate, lauryl myristate, isopropyl palmitate, diisopropyl sebacate and diisopropyl adipate. Further and very suitable ester oils include glyceride oils and in particular triglyceride oils derived from glycerol and fatty acids containing at least 6 carbons and especially natural oils.

Suitable liquid aromatic esters include fatty alkyl benzoates. Examples of such esters include suitable $C_8$ to $C_{18}$ alkyl benzoates or mixtures thereof, including in particular $C_{12}$ to $C_{15}$ alkyl benzoates, e.g., those available under the trademark Finsolv. An aryl benzoate, such as benzyl benzoate can also be used. Yet other suitable ester oils include oils in which a short alkylene group of 1 to 3 carbons, optionally substituted by a methyl group, is interposed between benzene and benzoate residues.

The total proportion of ester oils, including both aliphatic and aromatic ester oils (but exclusive of fragrance oil, which is typically a complex mixture of fragrance constituents from a number of different chemical classes; thus, while part of the carrier mixture, for convenience, fragrance oil is not broken down to its individual constituents, when considering carrier oil components) is commonly from 0 to 50% by weight of the carrier oil. In some embodiments the ester oil is present in an amount of from 5 to 30% by weight of the carrier oil. When both aromatic ester oil and aliphatic ester oil are present, the weight ratio of aromatic ester oil to aliphatic ester oil is often selected in the range of from 1:1 to 20:1.

Natural oils may also be employed in the subject carrier oils. Suitable natural oils include, for example, glyceride oils of unsaturated fatty acids. In many instances, the oils comprise one or more triglycerides. The fatty acid residues in the oils can comprise, commonly, from one to three olefinic unsaturated bonds and often one or two. If two or three olefinic unsaturated bonds are present, they can be conjugated. The fatty acid can also be substituted by a hydroxyl group. The natural oils employable herein desirably comprise one or more triglycerides of oleic acid, linoleic acid, linolenic acid or ricinoleic acid. Various isomers of such acids often have common names, including linolenelaidic acid, trans 7-octadecenoic acid, parinaric acid, pinolenic acid, punicic acid, petroselenic acid and stearidonic acid. It is especially desirable to employ glycerides derived from oleic acid, linoleic acid or petroselenic acid, or a mixture containing one or more of them.

Natural oils containing one or more of such triglycerides include coriander seed oil for derivatives of petroselinic acid, impatiens balsimina seed oil, parinarium laurinarium kernel fat or sabastiana brasilinensis seed oil for derivatives of cis-parinaric acid, dehydrated castor seed oil, for derivatives of conjugated linoleic acids, borage seed oil and evening primrose oil for derivatives of linoleic and linolenic acids, aquilegia vulgaris oil for columbinic acid and sunflower oil, olive oil or safflower oil for derivatives of oleic acid, often together with linoleic acids. Other suitable oils are obtainable from hemp, which can be processed to derive stearidonic acid derivatives and maize corn oil. An especially convenient natural oil by virtue of its characteristics and availability comprises sunflower oil, ranging from those rich in oleic acid glycerides to those rich in linoleic acid glycerides, rich indicating that its content is higher than that of the other named acid.

When present, glyceride oils typically represent from 1 to 8% by weight, more particularly from 1 to 5% by weight of the base composition. In one embodiment of interest glyceride oil is employed in the base composition together with a polyethylene glycol humectant in a weight ratio of from 3:1 to 1:3 and, more particularly from 3:2 to 2:3. It is especially desirable to employ in such combinations polyethylene glycol having an average (weight average) molecular weight of up to 420 Daltons.

A further class of suitable carrier oils comprise non-volatile liquid aliphatic ethers derived from at least one fatty alcohol that desirably contains at least 10 carbon atoms, such as myristyl ether derivatives e.g. PPG-3 myristyl ether or lower alkyl ($C_1$ to $C_6$) ethers of polyglycols (preferably polypropylene glycol and especially 10 to 20 units, such as an ether named as PPG-14 butyl ether in the CTFA. Such ethers, and especially those having a refractive index of above 1.46 can assist in masking the visibility of deposits on the skin, thereby complementing the positive skin conditioning properties of the overall composition. It can be very desirable to select the ether in a weight ratio to the AP active of at least 0.3:1 such as up to 0.8:1, one practical range being from 0.5:1 to 0.7:1. It is often convenient of the aliphatic ether to constitute at least 10%, and especially at least 15% and particularly up to 50% or more of the carrier oil.

A further class of carrier oils that can be employed herein comprises water-immiscible aliphatic alcohols, and particularly those having a boiling point of higher than 100° C. These include branched chain alcohols of at least 10 carbon atoms and in many instances up to 30 carbon atoms, particularly 15 to 25, such as isostearyl alcohol, hexyl-decanol and octyl-dodecanol. It will be recognized that octyl dodecanol is of particular interest because it not only acts as an emollient oil but additionally moisturizes skin by the mechanism of occlusion. Other suitable water-immiscible alcohols include intermediate chain length linear alcohols, commonly containing from 9 to 13 carbon atoms, such as decanol or dodecanol.

When present, such alcohols can often constitute up to 5%, more particularly up to 3% by weight of the carrier oil.

The instant compositions preferably contain fragrance oil. Commonly, such fragrance oils contain at least 10 and often at least 20 fragrance components that are blended together to produce a perfume that is pleasing to the user of the composition. The fragrance constituents are normally a complex mixture of chemical classes including, for example, ester, ether and alcohol classes. When present, the amount of fragrance oil is normally from 0 to 15% by weight of the antiperspirant base, often constituting up to 10% by weight and especially at least 3% by weight thereof.

The anhydrous aerosol compositions herein are preferably at least substantially free from water-miscible monohydric alcohols, that is to say the aerosol composition contains less than 5%, especially less than 3% and more particularly less than 1% of such an alcohol, for example an aliphatic monohydric alcohol containing up to 6 carbons such as ethanol and/or propanol, and most particularly contains none at all. In some countries, ethanol is classified as a volatile organic compound, and its presence may count against the permitted levels of VOC.

In at least some embodiments, it is desirable that the aerosol composition is at least substantially free or virtually completely free from dihydric alcohols such as propylene glycol and related C3 to C6 glycols, exclusive of dihydric alcohols in bound or complexed form, for example, as in complexes of propylene glycol with AP active. In one embodiment, the total amount of such free dihydric alcohol in the aerosol antiperspirant composition is not greater than 1% by weight, and advantageously is none at all. By avoidance or limitation on the amount of such glycols, the potential deleterious effects of including them in the aerosol composition, for example, imparting stickiness upon application, are lessened or avoided.

It is desirable for the antiperspirant composition to comprise a suspending aid. Suitable suspending agents include colloidal silicas and clays. Non-limiting examples of suitable silicas include pyrogenic silicas and non-limiting examples of suitable clays include montmorillonite clays, such as bentonites and hectorites. Preferably, the suspending aids have hydrophobically treated surfaces. A particularly preferred bentonite is hydrophobic bentonite (e.g., aids which are commercially available under the trade mark Bentone, e.g., Bentone LT, Bentone 14, Bentone 27, Bentone 34, and Bentone 38/38V), a bentonite treated with hydrophobic cationic materials. Other suitable clay suspending aids include colloidal magnesium aluminum silicates. Advantageously, the suspending aid is utilized at a level of at least 0.05%, and preferably 0.1% by weight of the base composition, often up to 5% of the base composition. In at least one embodiment of interest, suspending aid is present in an amount of 0.1 to 1% of the base composition.

It can be advantageous to employ an activator in conjunction with a clay suspending aid, for example propylene carbonate. The amount of activator is commonly in the range of from 2 to 75% of the weight of the suspending aid.

The instant compositions can include one or more additional optional constituents which have hither to been incorporated or proposed for incorporation in antiperspirant compositions. Such optional constituents may be liquid (in which event they form part of the carrier oil mixture) or solid, and normally comprise in total not more than 10% and often not more than 5% by weight of the base composition. Such optional constituents can comprise non-antiperspirant deodorant actives, such as antimicrobial actives such as polyhexamethylene biguanides, e.g. those available under the trade name Cosmocil™ or chlorinated aromatics, e.g. triclosan available under the trade name Irgasan™, non-microbicidal deodorant actives such as triethylcitrate, bactericides and bacteriostats. Yet other deodorant actives can include zinc salts such as zinc ricinoleate. The compositions can additionally or alternatively contain as bacteristat an iron chelator such as pentenoic acid which hinders bacterial growth/reproduction. The proportion of the deodorant active in the base composition is often selected in the range of from about 0.05 to 2% by weight of the base composition and especially from 0.1 to 0.5%.

Yet other optional ingredients can include sensory modifiers, such as talc or finely divided polyethylene, such as in an amount of up to 3% by weight of the base composition; colorants, by way of non-limiting example in a proportion of up to 0.5% of the base composition; skin cooling agents such as menthol often selected in an amount of up 0.5%, particularly up to 0.2% of the base composition, and wash-off agents such as non-ionic surfactants, and particularly polyethoxylated fatty alcohols or acids, for example in an amount of up to about 3% of the base composition.

The anhydrous aerosol compositions used as part of the present invention comprise a propellant in addition to the base composition described above. In the subject compositions the weight ratio of propellant to antiperspirant base is in a range of from 2:1 to 4:1. In preferred embodiments the weight ratio of propellant to antiperspirant base is in a range of from 2:1 to 3.5:1, more preferably from 2.5:1 to 3.5:1.

Propellants suitable for use herein conveniently are low boiling point gases liquefied by compression. Such gases typically boil below −5° C., and often below −15° C., with alkanes and/or halogenated hydrocarbons being of particular interest. Examples of suitable alkanes are propane, butane and isobutane, often in varying admixtures of the three components, possibly containing a fraction of pentane or isopentane. Examples of halogenated hydrocarbons are fluorocarbons and chlorofluorocarbons such as, for example, 1,1-difluoroethane, 1-trifluoro-2-fluoroethane, dichlorodifluoromethane, 1-chloro-1,1-difluoroethane, and 1,1-dichloro-1,1,2,2-tetrafluoroethane. In one embodiment, the propellant comprises a hydrofluorocarbon propellant known as propellant 152a and, more particularly, comprises a mixture of hydrocarbon and hydrofluorocarbon propellant such as, for example, a mixture comprising butane and propellant 152a, which mixture possibly contains a fraction of isobutane and/or other hydrocarbons.

Of interest in the practice of this invention are propellants having standard vapor pressures in a range of 35 to 70 psi at 21° C., more particularly from 35 to 50 psi at 21° C. From a sensory perspective, propellant having a standard vapor pressure of 35-45 psi at 21° C. can be of particular interest. In one or more embodiments the propellant has a standard vapor pressure of 40-45 psi at 21° C.

The aerosol dispenser used in accordance with the invention comprises a container body, an aerosol valve, and a valve actuator. The aerosol valve typically seals a pressurized container body and the valve actuator is used to open the valve and release the antiperspirant composition contained within.

In typical embodiments, the dispenser comprises a spray channel leading from the aerosol valve and culminating in a spray orifice from which the composition emerges as a spray. The spray orifice may be associated with a swirl chamber, such as those conventionally used in the art.

The container body may be fabricated in any of a number of sizes as would be suitable for the particular product volume employed. For easy single handed operation product volumes of interest typically will not exceed 400 ml, with volumes of 75 to 350 ml and, more particularly, 15 to 125 ml being of particular interest. Conveniently, the container body is made from plastic, steel or aluminum. In at least one embodiment, the container body is aluminum.

The concentrated aerosol of the subject invention may be fabricated to have a pack life comparable to a conventional, non-concentrated aerosol product, in which case, the concentrate aerosol will employ a smaller volume can than the conventional, non-concentrated product. The concentrates may also be fabricated to have a product volume comparable to that of conventional, non-concentrated aerosol products, in which case the pack life of the concentrate will be considerably longer than that of the conventional, non-concentrated product.

The aerosol valve is attached to the container body, typically via a mounting cup affixed to the container rim. A sealing means such as, for example, a shrink resistant gasket, may be used to prevent leakage between the mounting cup and the container rim. The valve generally comprises a housing, valve chamber and stem, the stem having one or more orifices entering into same. In one preferred embodiment, the stem has a single stem orifice. A stem having a single stem orifice configured as a circular orifice having a diameter of from 0.4 to 0.6 mm and, more particularly, approximately 0.5 mm, is of particular interest in one or more embodiments, The invention contemplates other stem orifice configurations that provide valves capable of delivering the spray rates required of this invention.

The antiperspirant composition typically passes from the container into the valve via a dip tube. In the practice of this invention, the use of a dip tube having an inner diameter of from 3 mm to 4 mm and preferably from 3 mm to 3.5 mm may aid in controlling spray rate and avoiding spluttering.

An essential feature of the present invention is that the aerosol valve comprises a vapour phase tap (VPT). Such VPTs enable propellant from the headspace above the antiperspirant composition to enter a valve chamber and enhance spray formation and quality. A further essential feature of the present invention is that the aerosol valve comprises a restrictive tailpiece (RTP). Such RTPs connect a dip tube going into the antiperspirant composition with the main valve housing. The RTP may be an integral part of the valve housing.

The VPT and RTP are typically tubular in nature and each has an internal cross-sectional area. The present inventors have found that the ratio of these internal cross-sectional areas is critical to the effectiveness of present invention. This ratio, referred to as the VPT to RPT ratio, needs to be from 0.6:1 to 1.2:1 and more particularly from 0.7:1 to 1:1.

When the VPT and/or RTP varies in internal cross-sectional area along its length, the ratio of the two should be understood to refer to the ratio at the minimum cross-sectional area of each.

The valve component of the subject dispenser is typically configured to aid in providing the product with a mean spray rate of 0.3 to 0.55 g/s, more particularly 0.3 g/s to 0.5 g/s and especially 0.35 to 0.45 g/s.

The maximum diameter of the VPT is preferably less 0.75 mm and more preferably less than 0.65 mm.

The maximum diameter of the RTP is preferably less 0.8 mm and more preferably less than 0.7 mm.

At the preferred small RTP diameters, it is particularly important that the efficacy of the AP active is high, since it is difficult to avoid blockage of such orifices when using higher levels of less efficacious actives. For this reason, use of the AP active as described herein is particularly relevant when the RTP is less than 0.8 mm and especially so when the RTP is less than 0.7 mm.

Using the AP active as described herein together with the specified valve parameters enables higher efficacy concentrated aerosol compositions to be sprayed than ever before. Particularly with the preferred low RTPs discussed above, it is difficult to have high levels of AP active without blockage becoming a problem, but with the high efficacy AP actives as described herein, this problem is circumvented.

The valve actuator commonly comprises a spray channel and exit orifice, which orifice is frequently configured as part of a separately fabricated insert. The exit orifice is commonly from 200 to 800 microns in diameter. With the spray rates of the subject invention, to minimize blockage an exit orifice of 400 to 600 micron diameter may be desirable. Exit orifice diameters of from 450 to 550 microns are of particular interest in one or more embodiments.

The actuator also commonly includes a fingerpad or other activation means. The valve is typically biased to a closed position by means of a spring, also referred to as a sealing spring. Depressing the fingerpad, or other activation of the actuator, pushes down on the sealing spring, opening the valve and allowing the pressurized antiperspirant composition to exit the container through the valve stem. The exiting antiperspirant composition enters the spray channel and passes through the exit orifice, as an aerosol spray.

The product may further include packaging that, at the point of sale, educates consumers as to one or more benefits of the product, for example, pack life, efficacy, and/or sensory benefits. With respect to pack life, the product may include a comparison of the pack life of the product to other aerosol antiperspirants, including for example, aerosol antiperspirant products other than concentrated products as herein described. Suitable forms for packaging include, for example, primary packaging, secondary packaging, labels, inserts, and the like. Alternatively and/or additionally, such information may be conveyed by other media, for example, advertising, marketing campaigns, and the like.

An aerosol product according to the present invention can be made by first blending together the ingredients of the base composition in a vessel, less any ingredient intended to be added later, agitating the mixture to suspend the particulate AP active, charging an aerosol container body with the mixed base composition and separately charging any other ingredient not blended previously into the base composition, charging either before, after or simultaneously, fitting and sealing a discharge line containing the valve onto the aerosol container body and injecting propellant gas into the container body through the discharge line.

The antiperspirant aerosol composition of the instant invention can be sprayed onto skin and particularly into the underarm (axilla) in a conventional manner for spraying liquid compositions. The container body is desirably held at a distance of between 12 and 18 cm from the armpit and the valve in the discharge line opened. The composition can be sprayed at the discretion of the user for a conventional period of time, typically on the order of one half to two seconds per armpit.

In one embodiment of particular interest, the concentrated aerosol antiperspirant product has a mean spray rate of from 0.40 g/sec to 0.48 g/sec, a ratio of propellant to antiperspirant base of from 2.5:1 to 3.5:1, and a ratio of propellant to AP active of from 6:1 to 9:1.

Except in the operating and comparative examples, or where otherwise explicitly indicated, all numbers in this description indicating amounts or ratios of materials, conditions of reaction; physical properties of materials and/or use; dimensions and dimension ratios, are to be understood as modified by the word "about".

The term "comprising" is meant not to be limiting to any subsequently stated elements but rather to encompass non-specified elements of major or minor functional importance. Whenever the words "including" or "having" are used, these terms are meant to be equivalent to "comprising" as defined above.

It should be noted that in specifying any range of concentration or amount, any particular upper concentration or amount can be associated with any particular lower concentration or amount.

All parts, percentages, ratios, and proportions referred to in the subject specification and in the appended claims are by weight unless otherwise indicated.

The following Examples will more fully illustrate the embodiments of this invention. The examples are not intended to limit the scope of the invention in any manner.

EXAMPLES

In the following examples, all parts, percentages and ratios are by weight unless indicated otherwise.

The AASCH AP active as detailed in Table 1 may be prepared by the following process. 15 parts of Reach 301 powder, 0.9 parts anhydrous calcium chloride and 2.0 parts glycine are combined with 75.9 parts water at room temperature. The solution is heated at 85° C. for 18 hours in sealed 1 L jars. The resulting solution is spray-dried using a bench-top Lab-Plant-05 spray dryer (inlet temperature 250°, outlet temperature 112+/−1°, jet atomisation).

The particulate AASCH obtained from the above process would typically have a mean (D50) particle size of from 5 to 10 microns.

Compositions as described in Table 1 may be prepared by the following procedure. The antiperspirant base is prepared by charging a vessel with the base's liquid and solid components in the amounts specified in Table 1 and agitating the resulting mixture until the AASCH AP active is suspended. The base composition is introduced into an aluminum container that is fitted with a commercially available valve having a single internal metering orifice, a vapor phase tap, a VPT to RTP ratio as indicated, and a dip tube of 3.2 mm inner diameter. The container is sealed and pressurized to an internal pressure as indicated by injection of a hydrocarbon propellant (propane, butane and isobutane [CAP-40™, ex Calor]) in a ratio of propellant to antiperspirant base as indicated.

TABLE 1

| | Example | | |
| --- | --- | --- | --- |
| | 1 | 2 | 3 |
| Component | | Wt. % | |
| AASCH (AP active) | 9.4 | 8.1 | 6.9 |
| Volatile Silicone (D5) | 6.0 | 5.3 | 6.3 |
| PPG-14 butyl ether | 5.6 | 4.8 | 4.8 |
| Hydrophobically modified clay | 1.0 | 0.8 | 0.7 |
| Fragrance* | 2.4 | 2.0 | 2.0 |
| CAP 40 (propellant) | 75.6 | 79.0 | 79.3 |
| CAP40:AASCH | 8.0:1 | 9.8:1 | 11.5:1 |
| CAP:Antiperspirant Base | 3.1:1 | 3.8:1 | 3.8:1 |
| VPT diameter (mm) | 0.5 | 0.64 | 0.64 |
| RPT diameter (mm) | 0.5 | 0.76 | 0.76 |
| VPT:RTP | 1:1 | 0.7:1 | 0.7:1 |

*Also includes a small amount (0.02-0.03% propylene carbonate).

The invention claimed is:

1. An antiperspirant aerosol product having a mean spray rate of from 0.35 g/s to 0.55 g/s and comprising:
A) an anhydrous antiperspirant aerosol composition containing less than 0.5% by weight water and comprising a propellant and a base composition comprising particulate antiperspirant active suspended in a carrier oil, the ratio of propellant to base composition being from 2:1 to 4:1 by weight, the ratio of propellant to particulate antiperspirant active being from 5:1 to 10:1 by weight and
B) an aerosol dispenser comprising: a container body, an aerosol valve, and a valve actuator;
wherein the particulate antiperspirant active comprises a basic aluminium chloride compound of formula $Al_2(OH)_{4.4}Cl_{1.6}$ to $Al_2(OH)_{4.9}Cl_{1.1}$, a water soluble calcium salt and an amino acid; and the aerosol valve of the aerosol dispenser has a vapor phase tap (VPT) to restrictive tailpiece (RTP) ratio of from 0.6:1 to 1.2:1, this ratio relating to the minimum cross-sectional area of each, and wherein the diameter of the RTP is less than 0.8 mm.

2. The antiperspirant aerosol product according to claim 1, wherein the antiperspirant active is activated aluminium sesquichlorohydrate (AASCH) prepared by heat activation of aluminium sesquichlorohydrate (ASCH) with a water soluble calcium salt and an amino acid.

3. The aerosol antiperspirant product according claim 1, wherein the ratio of carrier oil to antiperspirant active is from 1.2:1 to 2:1 by weight.

4. The aerosol antiperspirant product according to claim 1, having a VPT to RTP ratio of 0.7:1 to 1.1:1.

5. The aerosol antiperspirant product according to claim 1, wherein the carrier oil comprises volatile silicone oil.

6. The aerosol antiperspirant product according to claim 1, wherein the carrier oil comprises non-volatile oil.

7. The aerosol antiperspirant product according to claim 1, wherein the diameter of the RTP is less than 0.7 mm.

8. The aerosol antiperspirant product according to claim 1, having a mean spray rate of from 0.35 g/s to 0.45 g/s.

9. The aerosol antiperspirant product according to claim 1, wherein the ratio of propellant to antiperspirant active is from 6:1 to 9:1.

10. The aerosol antiperspirant product according to claim 1, wherein the ratio of propellant to antiperspirant base composition is 2:1 to 3.5:1.

11. The aerosol antiperspirant product according to claim 1, wherein the anhydrous antiperspirant aerosol composition is free of ethanol.

* * * * *